United States Patent [19]

Tanaka et al.

[11] Patent Number: 5,545,647
[45] Date of Patent: Aug. 13, 1996

[54] 3-PHENYLPYRROLIDINE DERIVATIVES

[75] Inventors: Toshihiko Tanaka; Akihiro Yamamoto; Akira Amenomori, all of Kanagawa-ken, Japan

[73] Assignee: Mitsubishi Chemical Corporation, Tokyo, Japan

[21] Appl. No.: 399,341

[22] Filed: Mar. 6, 1995

[30] Foreign Application Priority Data

Mar. 8, 1994 [JP] Japan ..................... 6-037187

[51] Int. Cl.$^6$ ............. A61K 31/395; C07D 207/04
[52] U.S. Cl. ............. 514/343; 514/85; 514/89; 514/91; 514/94; 514/95; 514/99; 514/247; 514/255; 514/300; 514/307; 514/326; 514/397; 514/406; 514/422; 514/423; 514/424; 514/414; 548/111; 548/112; 548/119; 548/364.1; 548/314.7; 548/412; 548/413; 548/467; 548/517; 548/527; 548/518; 548/530; 548/537; 548/538; 548/542; 546/21; 546/22; 546/23; 546/337; 546/122; 546/146; 546/208; 546/279.1; 544/224; 544/232; 544/406; 546/256; 546/278.4
[58] Field of Search .................... 548/530, 537, 548/538, 542, 111, 112, 119, 412, 413, 314.7, 364.1, 518, 467, 517, 527; 514/423, 424, 85, 89, 91, 94, 95, 99, 397, 406, 422, 307, 300, 326; 546/21, 22, 23, 337, 146, 281, 122, 208; 544/232

[56] References Cited

FOREIGN PATENT DOCUMENTS

| | | |
|---|---|---|
| 0511865 | 11/1992 | European Pat. Off. . |
| 2264531 | 10/1975 | France . |
| 550787 | 6/1974 | Switzerland . |
| WO91/16303 | 10/1991 | WIPO . |
| WOA91/15451 | 11/1991 | WIPO . |
| WO92/19594 | 11/1992 | WIPO . |

OTHER PUBLICATIONS

CA87:39271K4–(Polyalkoxyphenyl)–2–pyrrolidinones. Huth et al., (1975).

CAS–Registry Handbook, 1977, Suppl. (StN Database) RN:63140–31–8.

*Primary Examiner*—Joseph K. McKane
*Attorney, Agent, or Firm*—Wenderoth, Lind & Ponack

[57] ABSTRACT

3-Phenylpyrrolidine compounds of the formula

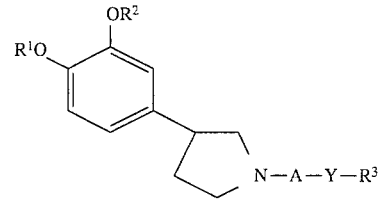

effectively inhibit phosphodiesterase (PDE) IV activities and can be used as medicaments for conditions such as asthma.

8 Claims, No Drawings

3-PHENYLPYRROLIDINE DERIVATIVES

FIELD OF THE INVENTION

The present invention relates to new 3-phenylpyrrolidine derivatives, and more specifically, to 3-phenylpyrrolidine derivatives ensuring inhibition of phosphodiesterase (PDE) IV activities, their optical isomers, salts, N-oxide derivatives, hydrates or solvates.

BACKGROUND OF THE INVENTION cAMP (cyclic adenosine 3',5'-monophosphate) is an important second messenger which participates in relaxing bronchial smooth muscles and regulating functions of inflammatory cells. cAMP is decomposed into inactive 5'-AMP by phosphodiesterase (PDE). Accordingly, if the decompostion by PDE is suppressed to increase intracellular concentrations of cAMP, it is considered that bronchial dilatation and anti-inflammatory effects can be obtained so that concerns have been running high for PDE inhibitors (suppressing decomposition of cAMP) as antiasthmatics. Further, recently, five kinds of PDE isozymes (PDE I, II, III, IV, V) have been identified and their tissue distributions have been revealed (Adv. Second Messenger Phosphoprotein Res., 22, 1 (1988), Trends Pharm., Sci., 11, 150 (1990)).

Among the inhibitors against these isozymes, possibility has been pointed out that the specific inhibitors of PDE IV are effective in treating asthma (Thorax, 26, 512 (1991)). As a compound having the specific inhibition of PDE IV, for example, a compound (rolipram xxx) disclosed in Japanese First (unexamined) Patent Publication No. 50-157360 is known as represented by the following formula:

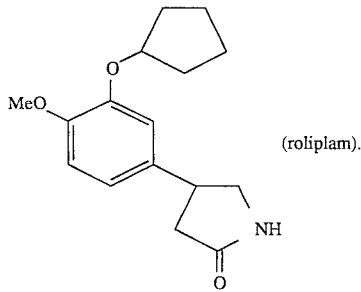

(roliplam).

Although various compounds are known other than the foregoing as disclosed in, such as, Japanese First (unexamined) Patent Publications No. 4-253945 and 5-117239, W09115451, W09207567, EP497564, W09219594, they have not been applied clinically up to date so that development of further useful compounds has been demanded.

In J. Pharm. Sci., 73, 1585 (1984), a compound represented by the following formula and its dopaminergic activity are described:

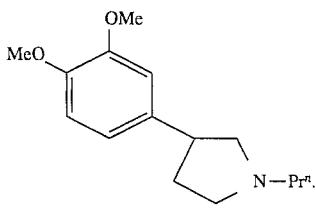

In Eur. J. Med., 27, 407 (1992), a compound represented by the following formula and its binding affinity at dopamine receptor are described:

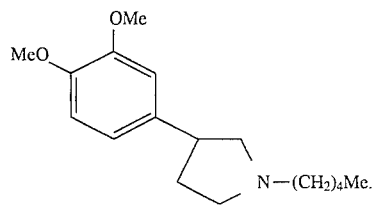

In J. Org. Chem., 58, 36 (1993), a compound represented by the following formula is described, while no description about its physiological activity is provided:

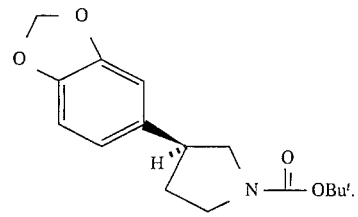

In Swiss Patent No. 526535, a compound represented by the following formula is described as a synthetic intermediate:

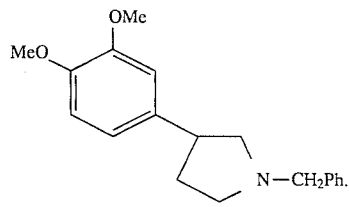

In Japanese Second (examined) Patent Publication No. 29-16871, a compound represented by the following formula is described as having antiulcer effect:

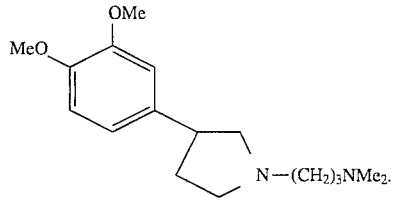

In Japanese First (unexamined) Patent Publication No. 50-157360, a compound represented by the following general formula is described as a treating medicament for neuropsychosis:

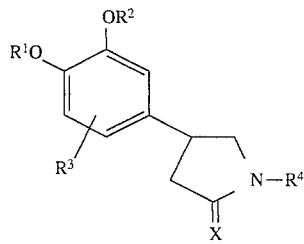

wherein R¹ and R² independently represent $C_1$–$C_5$ alkyl; R³ represents hydrogen or methoxy; R⁴ represents hydrogen, alkyl, aryl or acyl; and X represents oxygen or sulfur.

In Japanese Second (examined) Patent Publication No. 61-2660, a compound represented by the following general formula is described as a treating medicament for neuropsychosis:

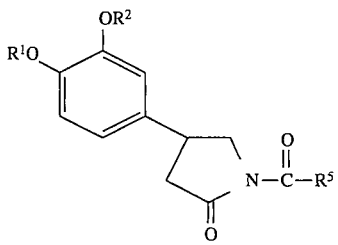

wherein R¹ and R² may be the same or different and independently represent $C_1$–$C_5$ alkyl; and R⁵ represents $C_1$–$C_8$ O-aralkyl, O-aryl, NH-aryl, NH-aralkyl, N-(alkyl)₂, N-(aryl)₂ or

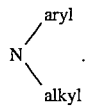

In Japanese First (unexamined) Patent Publication No. 2-121962, a compound represented by the following formula is described as having calcium antagonism:

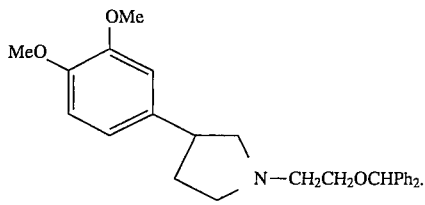

In European Patent No. 344577, a compound represented by the following formula is described as a treating medicament for ischemia heart disease:

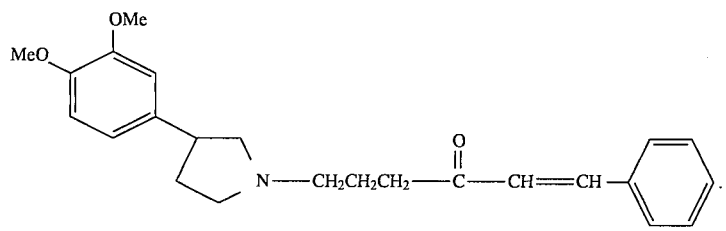

SUMMARY OF THE INVENTION

The present inventors have made researche for providing new compounds showing the inhibition of PDE IV and found out that specific 3-phenylpyrrolidine derivatives have excellent physiological activity, so as to reach completion of the present invention.

Specifically, the gist of the present invention resides in a 3-phenylpyrrolidine derivative of the following general formula (I):

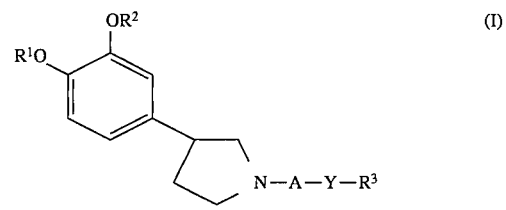

wherein R¹ represents $C_1$–$C_4$ alkyl; R² represents tetrahydrofuranyl, $C_1$–$C_7$ alkyl, $C_1$–$C_7$ haloalkyl, $C_2$–$C_7$ alkenyl, bicyclo [2,2,1]hept-2-yl or $C_3$–$C_8$ cycloalkyl; A represents

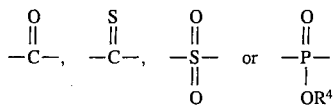

wherein R⁴ represents $C_1$–$C_4$ alkyl; Y represents —O—, —S—, —O—N=CH—, —NR⁵— wherein R⁵ represents hydrogen, $C_1$–$C_4$ alkyl, $C_2$–$C_4$ alkylcarbonyl or pyridylmethyl, or single bond; and R³ represents $C_1$–$C_7$ alkyl which is unsubstituted or substituted by one or more substituents, or —(CH₂)ₙ—X wherein n is an integer of from 0 to 4, X represents phenyl which is unsubstituted or substituted by one or more substituents, naphtyl which is unsubstituted or substituted by one or more substituents, or heterocyclic residue which is unsubstituted or substituted by one or more substituents; provided that when —A—Y—R³ is

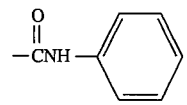

R¹ and R² are not methyl at the same time.

The gist of the present invention further resides in optical isomers, salts, N-oxide derivatives, hydrates and solvates of the foregoing 3-phenylpyrrolidine derivative, and further resides in a pharmaceutical composition including such a compound as an effective component.

DETAILED DESCRIPTION OF THE INVENTION

Hereinbelow, the present invention will be described in detail.

In the following general formula (I):

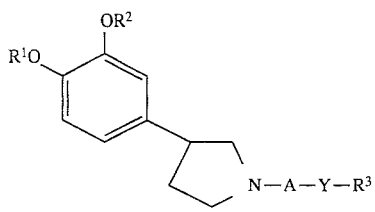

$R^1$ represents linear or branched $C_1$–$C_4$ alkyl (methyl, ethyl, n-propyl, isopropyl, n-butyl, isobutyl, sec-butyl, t-butyl or the like), preferably methyl or ethyl, and more preferably methyl.

$R^2$ represents tetrahydrofuranyl, linear or branched $C_1$–$C_7$ alkyl (methyl, ethyl, n-propyl, isopropyl, n-butyl, isobutyl, sec-butyl, t-butyl, n-butyl, n-pentyl, 1,2-dimethylpropyl, 1,1-dimethylpropyl, n-hexyl, 1-methylpentyl, 2-methylpentyl, 3-methylpentyl, 4-methyl pentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, heptyl, 5-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl or the like), $C_1$–$C_7$ haloalkyl (chloromethyl, bromomethyl, dichloromethyl, 1-chloroethyl, 2-chloroethyl, 3-chloropropyl, 4-chlorobutyl, 5-chloropentyl, 6-chlorohexyl, difluoromethyl, trifluoromethyl or the like), $C_2$–$C_7$ alkenyl (vinyl, allyl, 2-propenyl, isopropenyl, 3-butenyl, 4-pentenyl, 5-hexenyl or the like), bicyclo [2,2,1]hept-2-yl, or $C_3$–$C_8$ cycloalkyl (cyclopropyl, cyclobutyl, cyclopentyl, cyclohexyl, cycloheptyl or the like), preferably tetrahydrofuranyl, $C_3$–$C_6$ alkyl or $C_4$–$C_6$ cycloalkyl, and more preferably cyclopentyl.

A represents

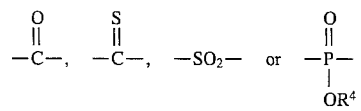

wherein $R^4$ represents linear or branched $C_1$–$C_4$ alkyl (methyl, ethyl, n-propyl, isopropyl, n-butyl, isobutyl, sec-butyl, t-butyl or the like), preferably

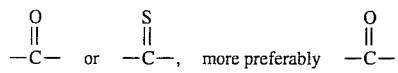

Y represents —O—, —S—, —O—N=CH—, —NR$^5$— where $R^5$ represents hydrogen, linear or branched $C_1$–$C_4$ alkyl (methyl, ethyl, n-propyl, isopropyl, n-butyl, isobutyl, sec-butyl, t-butyl or the like) or pyridylmethyl, or single bond, preferably —O—, —S—, —NR$^5$— ($R^5$ is as defined above) or single bond, and more specifically —O— or —NR$^5$— ($R^5$ is as defined above).

$R^3$ represents linear or branched $C_1$–$C_7$ alkyl (methyl, ethyl, n-propyl, isopropyl, n-butyl, isobutyl, sec-butyl, t-butyl or the like) which is unsubstituted or substituted by one or more substituents selected from the group consisting of halogen (fluorine, chlorine, bromine, iodine or the like), linear or branched $C_1$–$C_4$ alkoxy (methoxy, isopropoxy, butoxy or the like), linear or branched $C_1$–$C_4$ alkylthio (methylthio, isopropylthio, butylthio or the like), linear or branched $C_1$–$C_4$ alkylsulfinyl (methylsulfinyl, isopropylsulfinyl, butylsulfinyl or the like), linear or branched $C_1$–$C_4$ alkylsulfonyl (methylsulfonyl, isopropylsulfonyl, butylsulfonyl or the like), cyano, nitro, amino, hydroxy, carboxy, benzyloxy, $C_1$–$C_4$ acyl (formyl, acetyl, propionyl or the like), $C_2$–$C_4$ alkoxycarbonyl (methoxycarbonyl, ethoxycarbonyl or the like), linear or branched $C_1$–$C_4$ alkylamino (methylamino, isopropylamino, butylamino or the like), linear or branched $C_2$–$C_6$ dialkylamino (dimethylamino, diethylamino or the like), and

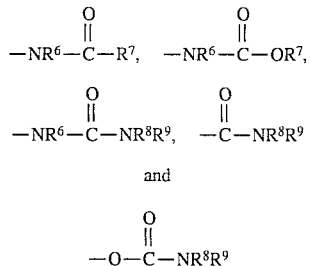

and $$-O-\overset{O}{\underset{\|}{C}}-NR^8R^9$$

wherein $R^6$, $R^8$ and $R^9$ independently represent hydrogen or linear or branched $C_1$–$C_4$ alkyl (methyl, ethyl, n-propyl, isopropyl, n-butyl, isobutyl, sec-butyl, t-butyl or the like) and $R^7$ represents linear or branched $C_1$–$C_4$ alkyl (methyl, ethyl, n-propyl, isopropyl, n-butyl, isobutyl, sec-butyl, t-butyl or the like), and preferably selected from the group consisting of halogen, $C_1$–$C_4$ alkoxy, hydroxy, $C_1$–$C_4$ alkylamino and $C_2$–$C_6$ dialkylamino; or —(CH$_2$)$_n$X wherein n is an integer of from 0 to 2, preferably from 0 to 2, and more preferably 1 or 2, and X represents phenyl, naphtyl or heterocyclic residue (thienyl, furyl, pyrrolyl, imidazolyl, pyrazolyl, triazolyl, tetrazolyl, pyridyl, pyrrolidinyl, piperidyl, piperidino, oxazolyl, isoxazolyl, thiazolyl, isothiazolyl, morpholinyl, morpholino, piperazinyl, pyridazinyl, pyrazinyl, pyrimidinyl, triazinyl, 1,2,3,4-tetrahydroquinoline-2-yl, 5,6,7,8-tetrahydro-1,6-naphthyridine-6-yl, indolyl or the like, which includes 1 to 4 a hetero atoms selected from oxygen, sulfur and nitrogen and 5 to 10 atoms in total for forming a ring, preferably thienyl, furyl, imidazolyl, pyrazolyl, pyridyl, pyrrolidinyl, piperidyl, piperidino, oxazolyl, isoxazolyl, thiazolyl, isothiazolyl, pyridazinyl, pyrazinyl, pyrimidinyl, 1,2,3,4-tetrahydroquinoline-2-yl, 5,6,7,8-tetrahydro-1,6-naphthyridine-6-yl, indolyl, and more preferably pyridyl, piperidyl, piperidino, piperazinyl, pyridazinyl, pyrazinyl, pyrimidinyl or the like, which has a 6-membered ring and includes 1 or 2 nitrogen atoms as hetero atom), and wherein each of phenyl, naphthyl or heterocyclic residue referred to above is unsubstituted or substituted by one or more substituents selected from the group consisting of halogen (fluorine, chlorine, bromine, iodine or the like), linear or branched $C_1$–$C_4$ alkyl (methyl, ethyl, n-propyl, isopropyl, n-butyl, isobutyl, sec-butyl, t-butyl or the like), linear or branched $C_1$–$C_4$ alkoxy (methoxy, isopropoxy, butoxy or the like), linear or branched $C_1$–$C_4$ alkylthio (methylthio, isopropylthio, butylthio or the like), linear or branched $C_1$–$C_4$ alkylsulfinyl (methylsulfinyl, isopropylsulfinyl, butylsulfinyl or the like), linear or branched $C_1$–$C_4$ alkylsulfonyl (methylsulfonyl, isopropylsulfonyl, butylsulfonyl or the like), cyano, nitro, amino, hydroxy, carboxy, $C_1$–$C_4$ acyl (formyl, acetyl, propionyl or the like), $C_2$–$C_4$ alkoxycarbonyl (methoxycarbonyl, ethoxycarbonyl or the like), linear or branched $C_1$–$C_4$ alkylamino (methylamino, isopropylamino, butylamino or the like), linear or branched $C_2$–$C_6$ dialkylamino (dimethylamino, diethylamino or the like),

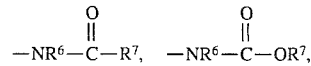

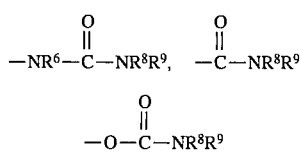

wherein $R^6$, $R^7$, $R^8$ and $R^9$ are as defined above,

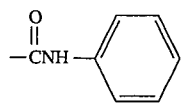

wherein $R^{10}$ represents linear or branched $C_1$–$C_4$ alkyl (methyl, ethyl, n-propyl, isopropyl, n-butyl, isobutyl, sec-butyl, t-butyl or the like) and R" represents $C_3$–$C_8$ cycloalkyl (cyclopropyl, cyclobutyl, cyclopentyl, cyclohexyl, cycloheptyl or the like) or linear or branched $C_1$–$C_4$ alkyl (methyl, ethyl, n-propyl, isopropyl, n-butyl, isobutyl, sec-butyl, t-butyl or the like), and pyridyl, and preferably selected from the group consisting of halogen, $C_1$–$C_4$ alkyl, $C_1$–$C_4$ alkoxy, cyano, nitro, amino, hydroxy, phenyl and pyridyl, and wherein X preferably represents heterocyclic residue which is unsubstituted or substituted by one or more substituents (as defined above), and more preferably heterocyclic residue which is unsubstituted.

In the general formula (I), when —A—Y—$R^3$ is $$-\overset{O}{\underset{\|}{C}}NH-\!\!\!\!\bigcirc$$

$R^1$ and $R^2$ are not methyl at the same time.

When $R^3$ represents —$(CH_2)_n$—X (n is as defined above) and B is heterocyclic residue having one or more nitrogen atoms as hetero atom, it is possible that the compounds represented by the general formula (I) exist in the form of N-oxide derivatives. On the other hand, it is preferable that salts of the compounds represented by the general formula (I) are physiologically acceptable so that, for example, inorganic acid salts, such as, a hydrochloride, a hydrobromide, a hydroiodide, a sulfate, a phosphate, and organic acid salts, such as, an oxalate, a maleate, a fumarate, a lactate, a malate, a citrate, a tartrate, a benzoate, a methanesulfonate, a p-toluenesulfonate can be enumerated. The compounds of the formula (I), their N-oxide derivatives and their salts can exist in the form of hydrates or solvates. Accordingly, those hydrates and solvates are also included in the compounds of the present invention. As solvents of solvates, methanol, ethanol, isopropanol, acetone, ethyl acetate, methylene chloride and the like can be enumerated.

Further, the compounds of the general formula (I) include asymmetric carbon atoms so that isomers exist. These isomers are also included in the present invention.

The compound of the present invention can be prepared, for example, according to the following method:

Preparation Method 1

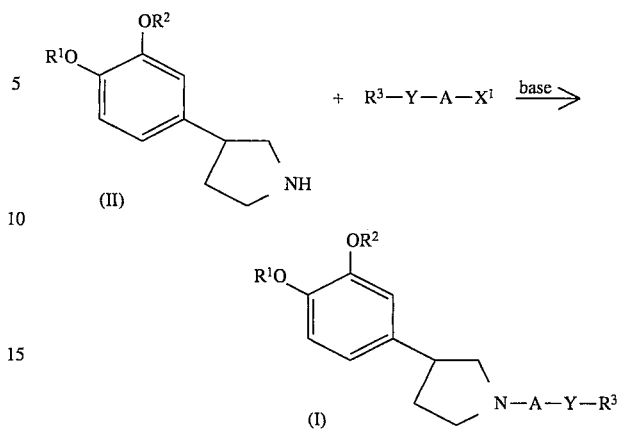

wherein $R^1$, $R^2$, $R^3$, A and Y are as defined before, and $X^1$ represents halogen.

The reaction is performed at a temperature range from 0° to 150° C. in the presence of organic base, such as, triethylamine, pyridine or N,N-diethylaniline or inorganic base, such as, sodium carbonate or sodium hydride, by use of no solvent or in a solvent, for example, ketones, such as, acetone or ethyl methyl ketone, aromatic hydrocarbones, such as, benzene or toluene, ethers, such as, diethyl ether, tetrahydrofuran or dioxane, acetic esters, such as, ethyl acetate or isobutyl acetate, or in an aprotic polar solvent, such as, acetonitrile, N,N-dimethylformamide, dimethyl sulfoxide or N-methylpyrrolidone.

A compound of the general formula (II) which is a starting material of the foregoing reaction can be prepared, for example, according to the following reaction formula from a compound of the following general formula (III) which are prepared according to the method described in Japanese First (unexamined) Patent Publication No. 50-157360 or the like.

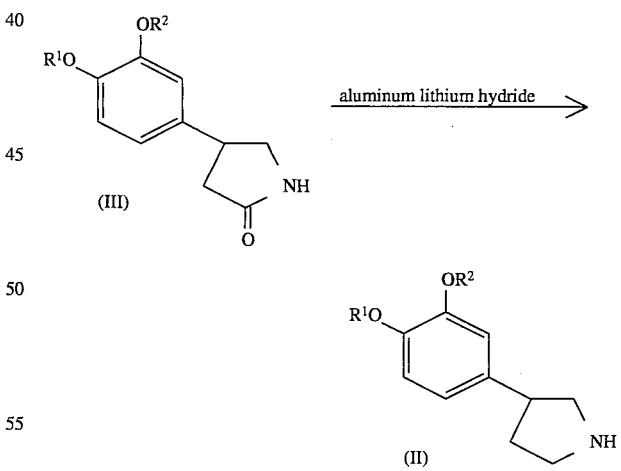

wherein $R^1$ and $R^2$ are as defined before.

Preparation Method 2

When A is

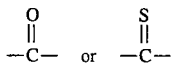

and Y represents —O—, —S—, —O—N=CH— or —NR⁵— (R⁵ is as defined before), a compound of the following general formula (V) can also be prepared according to the following method:

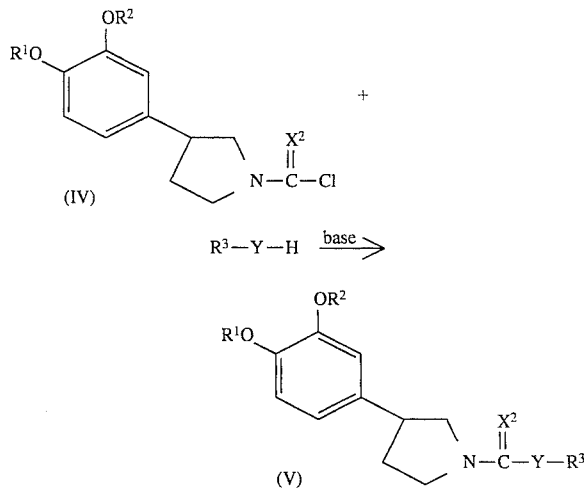

wherein $R^1$, $R^2$, $R^3$ and Y are as defined before, and $X^2$ represents oxygen or sulfur.

The reaction is performed at a temperature range from 0° to 150° C. in the presence of organic base, such as, triethylamine, pyridine or N,N-diethylaniline or inorganic base, such as, sodium carbonate or sodium hydride, by use of no solvent or in a solvent, for example, ketones, such as, acetone or ethyl methyl ketone, aromatic hydrocarbones, such as, benzene or toluene, ethers, such as, diethyl ether, tetrahydrofuran or dioxane, acetic esters, such as, ethyl acetate or isobutyl acetate, or in an aprotic polar solvent, such as, acetonitrile, N,N-dimethylformamide, dimethyl sulfoxide or N-methylpyrrolidone.

A compound of the foregoing general formula (IV) which is a starting material of the foregoing reaction can be prepared according to the following reaction formula from the starting material (II) in the preparation method 1.

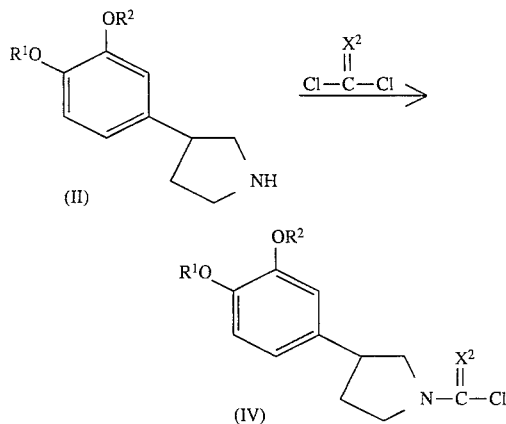

wherein $R^1$, $R^2$ and $X^2$ are as defined before.

When the compound of the present invention is used as a treating medicament, the compound is dosed singly or in combination with a pharmaceutically acceptable carrier. A composition of the carrier is determined based on solubility of the compound, chemical property of the compound, dosage route, dosage schedule and so on.

For example, the compound may be oral-dosed in the form of a granule medicine, a powder medicine, a tablet, a hard capsule medicine, a soft capsule medicine, a syrup medicine, an emulsion medicine, a suspended medicine or a liquid medicine, or may be intravenous-dosed, intramuscular-dosed or subcutaneous-dosed in the form of an injection medicine.

The compound may be powdered for injection and prepared to be used when necessary. The compound of the present invention may be used with pharmaceutical organic or inorganic and solid or liquid carrier or diluent which is suitable for oral, non-oral, through-body or local dosing. As a forming agent to be used when producing the solid medicine, for example, lactose, sucrose, starch, talc, cellulose or dextrin may be used. The liquefied medicines for oral dosing, that is, the emulsion medicine, the syrup medicine, the suspended medicine, the liquid medicine and the like, include the generally used inert diluent, such as, water or vegetable oil. These medicines can contain, other than the inert diluent, an auxiliary agent, such as, a wetting agent, a suspension assisting agent, a sweetening agent, an aromatic, a coloring agent or a preserving agent. The liquefied medicine may be contained in a capsule made of a material, such as, gelatin which can be disintegrated in the body. As a solvent or a suspending agent to be used in the course of producing the medicine for non-oral dosing, such as, the medicine for injection, for example, water, propylene glycol, polyethylene glycol, benzyl alcohol, ethyl oleate or lecithin can be enumerated. The known method can be used for making up the medicine.

When the compound of the present invention is used for oral dosing, a clinical dosing amount is, in general, 0.01 mg to 1000 mg per day, and preferably 0.01 mg to 100 mg, in case of an adult. It is naturally further preferable to properly increase or decrease a dosage amount depending on age, the condition of disease, the condition of patient, presence or absence of simultaneous dosing and so on. In case of the compound of the present invention, the foregoing dosing amount per day may be divided into two or three and dosed with proper intervals, or intermittent dosing may also be allowed.

On the other hand, when using the compound of the present invention as the injection medicine, it is preferable that a one-time dosage amount of 0.001 mg to 100 mg be continuously or intermittently dosed in case of an adult.

EMBODIMENT

Hereinbelow, the present invention will be described in detail in terms of embodiments and test examples. The present invention is not limited to those embodiments and tests.

EMBODIMENT 1

Preparation of 3-(3-cyclopentyloxy-4-methoxyphenyl)-1-(3-pyridylmethylaminocarbonyl) pyrrolidine (Compound No. 22 in Table 1):

216 mg of 3-(aminomethyl) pyridine and 202 mg of triethylamine were dissolved in 5 ml of tetrahydrofuran. During agitation at a cold temperature, a solution obtained by dissolving 545 mg of 1-chloroformyl-3-(3-cyclopentyloxy-4-methoxyphenyl) pyrrolidine in 3 ml of tetrahydrofuran was added in drops. After dropping, agitation was continued for 6 hours at a room temperature. Thereafter, the agitated solution was poured into ice water and then extracted with ethyl acetate. After organic layers were cleaned by water and dried over magnesium sulfate, it was concentrated under a reduced pressure. The residue was purified by means of the silica gel column chromatography to obtain 432 mg of Compound No. 22 in Table 1.

EMBODIMENT 2

Preparation of 3-(3-cyclopentyloxy-4-methoxyphenyl)-1-(ethoxycarbonyl) pyrrolidine (Compound No. 4 in Table 1):

460 mg of 3-(3-cyclopentyloxy-4-methoxyphenyl) pyrrolidine and 214 mg of triethylamine were dissoved in 15 ml of dichloromethane and cooled in an ice bath. During agitation, 229 mg of ethyl chloroformate was added in drops. After dropping, agitation was continued for 1 hour at a room temperature. Thereafter, the agitated solution was poured into ice water and then extracted with dichloromethane. After organic layers were cleaned by water and dried over magnesium sulfate, it was concentrated under a reduced pressure. The residue was purified by means of the silica gel column chromatography to obtain 92 mg of Compound No. 4 in Table 1.

EMBODIMENT 3

Compounds shown in Table 1 were synthesized according to the methods in Embodiments 1 and 2.

TABLE 1

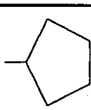

| compound No. | $R^1$ | $R^2$ | $-A-Y-R^3$ | physical properties |
|---|---|---|---|---|
| 1 | Me |  | $-\overset{O}{\underset{\|}{C}}-OBu^t$ | oily matter |
| 2 | Me |  | $-\overset{O}{\underset{\|}{C}}-Bu^t$ | oily matter |
| 3 | Me |  | $-\overset{O}{\underset{\|}{C}}-OCH_2-$ | oily matter |
| 4 | Me | 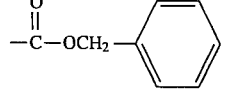 | $-\overset{O}{\underset{\|}{C}}-OEt$ | oily matter |
| 5 | Me |  | $-\overset{O}{\underset{\|}{C}}-CH_2Bu^t$ | oily matter |
| 6 | Me |  | $-\overset{O}{\underset{\|}{C}}-OBu^n$ | oily matter |
| 7 | Me |  | $-\overset{O}{\underset{\|}{C}}-$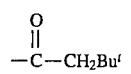 | oily matter |
| 8 | Me |  | $-\overset{O}{\underset{\|}{C}}-OBu^t$ | oily matter |
| 9 | Me |  | $-\overset{O}{\underset{\|}{C}}-$ | oily matter |

TABLE 1-continued

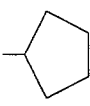

| compound No. | R¹ | R² | —A—Y—R³ | physical properties |
|---|---|---|---|---|
| 10 | Me | cyclopentyl | —C(=O)—CH₂—(3-pyridyl) | oily matter |
| 11 | Me | cyclopentyl | —C(=O)—NH—Bu$^t$ | mp 125–126° C. |
| 12 | Me | cyclopentyl | —C(=O)—NMe₂ | oily matter |
| 13 | Me | cyclopentyl | —C(=O)—OCH₂—(3-pyridyl) | oily matter |
| 14 | Me | cyclopentyl | —C(=O)—OCH₂—(3-pyridyl) · Me-C₆H₄-SO₃H | mp 148–149° C. |
| 15 | Me | cyclopentyl | —C(=O)—OCH₂—(3-pyridyl) · HCl | mp 108–114° C. |
| 16 | Me | cyclopentyl | —C(=O)—OCH₂—(3-pyridyl) · 1/2H₂SO₄ | mp 142–144° C. |
| 17 | Me | cyclopentyl | —C(=O)—OCH₂—(3-pyridyl N-oxide) | oily matter |
| 18 | Me | cyclopentyl | —C(=O)—OCH₂—(4-pyridyl N-oxide) | amorphous solid |
| 19 | Me | cyclopentyl | —C(=O)—OCH₂—(4-pyridyl) | oily matter |

TABLE 1-continued

| compound No. | R¹ | R² | —A—Y—R³ | physical properties |
|---|---|---|---|---|
| 20 | Me | cyclopentyl | —SO₂—(3-pyridyl) | oily matter |
| 21 | Me | cyclopentyl | —C(=O)—(pyrazinyl) | oily matter |
| 22 | Me | cyclopentyl | —C(=O)—NHCH₂—(3-pyridyl) | mp 129–130° C. |
| 23 | Me | cyclopentyl | —C(=O)—O—(3-pyridyl) | oily matter |
| 24 | Me | cyclopentyl | —C(=O)—OCH₂—(2-pyridyl) | oily matter |
| 25 | Me | cyclopentyl | —C(=O)—O—(3-pyridyl N-oxide) | oily matter |
| 26 | Me | cyclopentyl | —C(=O)—OCH₂—(2-pyridyl N-oxide) | oily matter |
| 27 | Me | cyclopentyl | —C(=O)—OCH₂—(N-methylpiperidin-3-yl) | oily matter |
| 28 | Me | cyclopentyl | —C(=O)—O—(4-pyridyl) | oily matter |
| 29 | Me | cyclopentyl | —C(=O)—OCH₂CH₂NMe₂ | oily matter |

TABLE 1-continued

| compound No. | R¹ | R² | —A—Y—R³ | physical properties |
|---|---|---|---|---|
| 30 | Me | cyclopentyl | —C(=O)—OCH₂CH₂OH | oily matter |
| 31 | Me | cyclopentyl | —P(=O)(OEt)₂ | oily matter |
| 32 | Me | cyclopentyl | —C(=O)—N(6,7-dimethoxy-1,2,3,4-tetrahydroisoquinolin-2-yl) | oily matter |
| 33 | Me | cyclopentyl | —C(=O)—C(Me)H—CH₂-(pyridin-3-yl) | oily matter |
| 34 | Me | cyclopentyl | —C(=O)—N(pyrrolidin-1-yl substituted with pyridin-3-yl) | oily matter |
| 35 | Me | Me | —C(=O)—OCH₂-(pyridin-3-yl) | oily matter |
| 36 | Me | cyclopentyl | —C(=O)—OCH₂CH₂-(pyridin-2-yl) | oily matter |
| 37 | Me | cyclopentyl | —C(=O)—OCH₂-(2-chloropyridin-4-yl) | oily matter |
| 38 | Me | cyclopentyl | —C(=O)—OCH₂-(6-chloropyridin-3-yl) | oily matter |
| 39 | Me | cyclopentyl | —C(=O)—O—N=CH-(pyridin-2-yl) | oily matter |
| 40 | Me | cyclopentyl | —C(=S)—OCH₂-(pyridin-3-yl) | oily matter |

TABLE 1-continued

| compound No. | R¹ | R² | —A—Y—R³ | physical properties |
|---|---|---|---|---|
| 41 | Me | 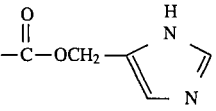 |  | oily matter |
| 42 | Me | 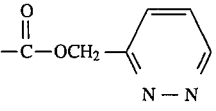 |  | oily matter |
| 43 | Me | 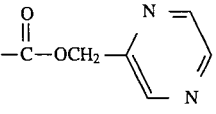 |  | oily matter |
| 44 | Me | 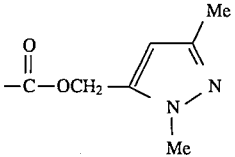 |  | oily matter |
| 45 | Me | 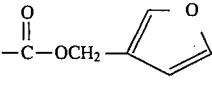 |  | oily matter |
| 46 | Me | 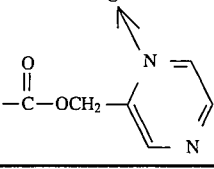 | | oily matter |

Hereinbelow, NMR spectra are shown for the following compounds in the form of amorphous solid and oily matter, wherein the compounds are identified by Compound No. in Table 1.

No. 1
$^1$HNMR (CDCl$_3$) δppm: 1.48 (s, 9H), 1.53–1.69 (m, 2 H), 1.73–2.00 (m, 7 H), 2.14–2.28 (m, 1H), 3.16–3.86 (m, 5H), 3.83 (s, 3H), 4.70–4.81 (m, 1H), 6.73–6.85 (m, 3H)

No. 2
$^1$HNMR (CDCl$_3$) δppm: 1.28 (s, 9H), 1.50–1.68 (m, 2 H), 1.73–2.04 (m, 7H), 2.13–2.33 (m, 1H), 3.16–4.10 (m, 5H), 3.83 (s, 3H), 4.71–4.80 (m, 1H), 6.71–6.85 (m, 3H)

No. 3
$^1$HNMR (CDCl$_3$) δppm: 1.52–1.65 (m, 2H), 1.76–2.05 (m, 7H), 2.18–2.36 (m, 1H), 3.24–3.92 (m, 5H), 3.82 (s, 3H), 4.72–4.79 (m, 1H), 5.16 (s, 2H), 6.74–6.83 (m, 3H), 7.24–7.38 (m, 5H)

No. 4
$^1$HNMR (CDCl$_3$) δppm: 1.24–1.31 (m, 3H), 1.54–1.70 (m, 2H), 1.74–2.04 (m, 7H), 2.18–2.32 (m, 1H), 3.22–3.90 (m, 5H), 3.83 (s, 3H), 4.12–4.22 (m, 2H), 4.77 (m, 1H), 6.74–6.84 (m, 3H)

No. 5
$^1$HNMR (CDCl$_3$) δppm: 1.08 (brs, 9H), 1.54–2.38 (m, 10H), 2.21 (brs, 2H), 3.22–4.06 (m, 5H), 3.83 (s, 3H), 4.70–4.80 (m, 1H), 6.75–6.81 (m, 3H)

No. 6
$^1$HNMR (CDCl$_3$) δppm: 0.90–0.98 (m, 3H), 1.34–2.04 (m, 13H), 2.18–2.32 (m, 1H), 3.24–3.92 (m, 5H), 3.82 (s, 3H), 4.08–4.13 (m, 2H), 4.76 (m, 1H), 6.74–6.83 (s, 3H)

No. 7
$^1$HNMR (CDCl$_3$) δppm: 1.56–1.70 (m, 2H), 1.76–2.42 (m, 8H), 3.24–3.94 (m, 5H), 3.83 (brs, 3H), 4.70–4.80 (m, 1H), 6.71–6.82 (m, 3H), 7.38–7.43 (m, 3H), 7.54–7.56 (m, 2H)

No. 8
$^1$HNMR (CDCl$_3$) δppm: 1.48 (s, 9H), 1.80–2.28 (m, 4H), 3.15–4.09 (m, 9H), 3.84 (s, 3H), 4.89–5.00 (m, 1H), 6.73 (brs, 1H), 6.84 (brs, 2H)

No. 9
$^1$HNMR (CDCl$_3$) δppm: 1.56–2.44 (m, 10H), 3.28–4.16 (m, 5H), 3.82 and 3.84 (a pair of s, 3H), 4.72–4.80 (m, 1H), 6.70–6.83 (m, 3H), 7.32–7.40 (m, 1H), 7.86–7.92 (m, 1H), 8.64–8.69 (m, 1H), 8.81 (m, 1H)

No. 10
¹HNMR (CDCl₃) δppm: 1.56–2.42 (m, 10H), 3.26–4.08 (m, 5H), 3.66 (brs. 2H), 3.83 (brs, 3H), 4.75 (m, 1H), 6.72–6.84 (m, 3H), 7.24–7.30 (m, 1H), 7.68–7.74 (m, 1H), 8.50–8.52 (m, 2H)
No. 12
¹HNMR (CDCl₃) δppm: 1.53–1.68 (m, 2H), 1.75–2.00 (m, 7H), 2.15–2.28 (m, 1H), 2.85 (s, 6H), 3.18–3.31 (m, 1H), 3.39 (t, 1H, J=9 Hz), 3.46–3.61 (m, 2H), 3.70 (d-d, 1H, J=7 and 9 Hz), 3.83 (s, 3H), 4.71–4.80 (m, 1H), 6.74–6.84 (m, 3H)
No. 13
¹HNMR (CDCl₃) δppm: 1.51–1.70 (m, 2H), 1.75–2.04 (m, 7H), 2.18–2.34 (m, 1H), 3.23–3.53 (m, 3H), 3.58–3.96 (m, 2H), 3.83 (s, 3H), 4.68–4.80 (m, 1H), 5.18 (s, 2H), 6.70–6.84 (m, 3H), 7.26–7.35 (m, 1H), 7.73 (m, 1H), 8.57 (m, 1H), 8.65 (m, 1H)
No. 17
¹HNMR (CDCl₃) δppm: 1.51–1.70 (m, 2H), 1.75–2.09 (m, 7H), 2.20–2.35 (m, 1H), 3.25–3.53 (m, 3H), 3.63–3.75 (m, 1H), 3.80–3.93 (m, 1H), 3.83 (s, 3H), 4.71–4.81 (m, 1H), 5.13 (brs, 2H), 6.70–6.86 (m, 3H), 7.27 (m, 2H), 8.16 (m, 1H), 8.28 (m, 1H)
No. 18
¹HNMR (CDCl₃) δppm: 1.54–2.08 (m, 9H), 2.22–2.36 (m, 1H), 3.28–3.92 (m, 5H), 3.83 (s, 3 H), 4.76 (m, 1H), 5.12 (brs, 2H), 6.75–6.84 (m, 3H), 7.27–7.32 (m, 2H), 8.17–8.21 (m, 2H)
No. 19
¹HNMR (CDCl₃) δppm: 1.56–2.12 (m, 9H), 2.24–2.36 (m, 1H), 3.30–3.90 (m, 5H), 3.83 (s, 3H), 4.77 (m, 1H), 5.19 (brs, 2H), 6.76–6.86 (m, 3H), 7.26–7.30 (m, 2H), 8.57–8.61 (m, 2H)
No. 20
¹HNMR (CDCl₃) δppm: 1.56–2.06 (m, 9H), 2.14–2.28 (m, 1H), 3.16–3.90 (m, 5H), 3.81 (s, 3H), 4.68–4.76 (m, 1H), 6.61–6.78 (m, 3H), 7.48–7.56 (m, 1H), 8.13–8.16 (m, 1H), 8.94 (brs, 1H), 9.10 (brs, 1H)
No. 21
¹HNMR (CDCl₃) δppm: 1.56–2.16 (m, 9H), 2.30–2.40 (m, 1H), 3.30–3.48 (m, 1H), 3.64–4.26 (m, 4H), 3.83 (brs, 3H), 4.74–4.80 (m, 1H), 6.77–6.83 (m, 3H), 8.52–8.56 (m, 1H), 8.62–8.66 (m, 1H), 9.17 (s, 1H)
No. 23
¹HNMR (CDCl₃) δppm: 1.56–2.18 (m, 9H), 2.26–2.42 (m, 1H), 3.34–4.16 (m, 5H), 3.83 (s, 3H), 4.72–4.80 (m, 1H), 6.78–6.88 (m, 3H), 7.32 (m, 1H), 7.55–7.60 (m, 1H), 8.47 (m, 2H)
No. 24
¹HNMR (CDCl₃) δppm: 1.50–1.70 (m, 2H), 1.73–2.04 (m, 7H), 2.20–2.35 (m, 1H), 3.25–3.59 (m, 3H), 3.66–3.78 (m, 1H), 3.83 (s, 3H), 3.86–3.96 (m, 1H), 4.70–4.79 (m, 1H), 5.28 (brs, 2H), 6.71–6.84 (m, 3H), 7.16–7.26 (m, 1H), 7.39 (t, 1H, J=7 Hz), 7.65–7.74 (m, 1H), 8.58 (m, 1H), 8.65 (m, 1H)
No. 25
¹HNMR (CDCl₃) δppm: 1.56–2.16 (m, 9H), 2.28–2.44 (m, 1H), 3.34–4.06 (m, 5H), 3.84 (s, 3H), 4.74–4.80 (m, 1H), 6.77–6.83 (m, 3H), 7.23–7.27 (m, 2H), 8.06–8.09 (m, 1H), 8.19 (s, 1H)
No. 26
¹HNMR (CDCl₃) δppm: 1.50–1.70 (m, 2H) 1.75–2.10 (m, 7H), 2.22–2.40 (m, 1H), 3.30–3.62 (m, 3H), 3.68–3.83 (m, 1H), 3.84 (s, 3H), 3.89–4.00 (m, 1H), 4.70–4.81 (m, 1H), 5.44 (brs, 2H), 6.74–6.86 (m, 3H), 7.20–7.35 (m, 2H), 7.36–7.45 (m, 1H), 8.25 (m, 1H)

No. 27 (diastereo mixture)
¹HNMR (CDCl₃) δppm: 1.52–2.40 (m, 17H), 2.27 and 2.29 (a pair of s, 3H), 2.78–2.94 (m, 2H), 3.24–4.08 (m, 7H), 3.83 (s, 3H), 4.72–4.80 (m, 1H), 6.75–6.86 (m, 3H)
No. 28
¹HNMR (CDCl₃) δppm: 1.56–1.72 (m, 2H), 1.76–1.94 (m, 6H), 2.04–2.16 (m, 1H), 2.33–2.42 (m, 1H), 3.34–3.93 (m, 5H), 3.83 (s, 3H), 4.73–4.80 (m, 1H), 6.32–6.38 (m, 2H), 6.75–6.86 (m, 3H), 7.72–7.77 (m, 2H)
No. 29
¹HNMR (CDCl₃) δppm: 1.51–1.69 (m, 2H), 1.74–2.01 (m, 7H), 2.15–2.30 (m, 1H), 2.29 (s, 3H), 2.31 (s, 3H), 2.60 (m, 2H), 3.22–3.50 (m, 3H), 3.57–3.72 (m, 1H), 3.75–3.91 (m, 1H), 3.82 (s, 3H), 4.22 (t, 2H, J=5 Hz), 4.70–4.80 (m, 1H), 6.71–6.84 (m, 3H)
No. 30
¹HNMR (CDCl₃) δppm: 1.51–1.69 (m, 2H), 1.74–2.05 (m, 7H), 2.19–2.34 (m, 1H), 2.80 (brs, 1H), 3.23–3.74 (m, 7H), 3.83 (s, 3H), 4.23–4.31 (m, 2H), 4.70–4.81 (m, 1H), 6.72–6.85 (m, 3H)
No. 31
¹HNMR (CDCl₃) δppm: 1.30–1.37 (m, 6H), 1.54–1.68 (m, 2H), 1.78–2.04 (m, 7H), 2.20–2.32 (m, 1H), 3.10–3.18 (m, 1H), 3.24–3.50 (m, 3H), 3.60–3.68 (m, 1H), 3.83 (s, 3H), 4.00–4.16 (m, 4H), 4.72–4.80 (m, 1H), 6.75–6.83 (m, 3H)
No. 32
¹HNMR (CDCl₃) δppm: 1.56–2.06 (m, 9H), 2.18–2.30 (m, 1H), 2.72–2.96 (m, 2H), 3.24–3.92 (m, 7H), 3.83 (s, 3H), 3.85 (s, 3H), 3.86 (s, 3H), 4.40 (s, 2H), 4.72–4.80 (m, 1H), 6.59 (s, 1H), 6.62 (s, 1H), 6.77–6.86 (s, 3H)
No. 33
¹HNMR (CDCl₃) δppm: 1.56–2.06 (m, 9H), 2.16–2.32 (m, 1H), 2.81 (s, 3H), 3.22–3.36 (m, 1H), 3.43 (t, 1H, J=9 Hz), 3.54–3.60 (m, 2H), 3.72–3.81 (m, 1H), 3.83 (s, 3H), 4.43 (d, 1H, J=12 Hz), 4.50 (d, 1H, J=12 Hz), 4.72–4.80 (m, 1H), 6.75–6.84 (m, 3H), 7.25–7.30 (m, 1H), 7.68–7.71 (m, 1H), 8.52–8.56 (m, 2H)
No. 34 (diastereo mixture)
¹HNMR (CDCl₃) δppm: 1.56–2.08 (m, 10H), 2.18–2.36 (m, 2H), 3.20–3.94 (m, 10H), 3.83 (s, 3H), 4.72–4.80 (m, 1H), 6.76–6.84 (m, 3H), 7.16–7.19 (m, 2H), 8.53–8.55 (m, 2H)
No. 35
¹HNMR (CDCl₃) δppm: 1.90–2.10 (m, 1H), 2.19–2.33 (m, 1H), 3.24–3.51 (m, 3H), 3.60–3.95 (m, 2H), 3.87 (s, 6H), 5.18 (brs, 2H), 6.70–6.86 (m, 3H), 7.27–7.34 (m, 1H), 7.68–7.76 (m, 1H), 8.57 (m, 1H), 8.65 (m, 1H)
No. 36
¹HNMR (CDCl₃) δppm: 1.56–2.06 (m, 9H), 2.16–2.28 (m, 1H), 3.12–3.88 (m, 7H), 3.83 (s, 3H), 4.48 (t, 2H, J=7 Hz), 4.75 (m, 1H) , 6.72–6.83 (m, 3H), 7.10–7.24 (m, 2H), 7.54–7.64 (m, 1H), 8.54 (m, 1H)
No. 37
¹HNMR (CDCl₃) δppm: 1.56–2.12 (m, 9H), 2.22–2.38 (m, 1H), 3.50–3.58 (m, 3H), 3.68–3.94 (m, 2H), 3.83 (s, 3H), 4.77 (m, 1H), 5.16 (brs, 2H), 6.76–6.85 (m, 3H), 7.12–7.21 (m, 1H), 7.31–7.33 (m, 1H), 8.34–8.38 (m, 1H)
No. 38
¹HNMR (CDCl₃) δppm: 1.51–1.68 (m, 2H), 1.73–2.04 (m, 7H), 2.19–2.33 (m, 1H), 3.23–3.52 (m, 3H), 3.57–3.92 (m, 2H), 3.83 (s, 3H), 4.70–4.80 (m, 1H), 5.15 (brs, 2H), 6.70–6.84 (m, 3H), 7.29–7.36 (m, 1H), 7.67–7.74 (m, 1H), 8.42 (m, 1H)
No. 39

¹HNMR (CDCl₃) δppm: 1.50–1.71 (m, 2H), 1.74– 2.11 (m, 7H), 2.23–2.40 (m, 1H), 3.30–3.64 (m, 3H), 3.70–3.85 (m, 1H), 3.84 (s, 3H). 3.90–4.05 (m, 1H), 4.71–4.83 (m, 1H), 6.73–6.85 (m, 3H), 7.33 (t, 1H, J=9 Hz), 7.76 (t, 1H, J=9 Hz), 8.14 (d, 1H, J=9 Hz), 8.43 (d, 1H, J=9 Hz), 8.64 (brs, 1H)

No. 40
¹HNMR (CDCl₃) δppm: 1.56–2.16 (m, 9H), 2.28–2.42 (m, 1H), 3.32–4.28 (m, 5H), 3.83 (brs, 3H), 4.72–4.78 (m, 1H), 5.56 and 5.57 (a pair of s, 2H) ,6.71–6.84 (m, 3H), 7.26–7.34 (m, 1H), 7.72–7.76 (m, 1H), 8.54–8.62 (m, 1H), 8.65–8.69 (m, 1H)

No. 41
¹HNMR (CDCl₃) δppm: 1.56–2.18 (m, 9H), 2.32–2.42 (m, 1H), 3.32–3.46 (m, 1H), 3.54–3.66 (m, 1H), 3.72–3.90 (m, 2H), 3.83 (s, 3H), 3.94–4.06 (m, 1H), 4.48 (brs, 1H), 4.60 (s, 2H), 4.72–4.80 (m, 1H) 6.75–6.85 (m, 3H), 7.28–7.30 (m, 1H), 8.02 (s, 1H)

No. 42
¹HNMR (CDCl₃) δppm: 1.56–2.08 (m, 9H), 2.22–2.36 (m, 1H), 3.26–3.56 (m, 3H), 3.66–3.96 (m, 2H), 3.83 (s, 3H), 4.72–4.80 (m, 1H), 5.50 and 5.51 (a pair of s, 2H), 6.75–6.84 (m, 3H), 7.46–7.53 (m, 1H), 7.58–7.66 (m, 1H), 9.14–9.16 (m, 1H)

No. 43
¹HNMR (CDCl₃) δppm: 1.56–2.10 (m, 9H), 2.20– 2.36 (m, 1H), 3.28–3.56 (m, 3H), 3.70–3.96 (m, 2H), 3.83 (s, 3H), 4.77 (m, 1H), 5.32 and 5.33 (a pair of s, 2H), 6.75–6.84 (m, 3H), 8.53–8.56 (m, 2H), 8.70–8.71 (m, 1H)

No. 44
¹HNMR (CDCl₃) δppm: 1.50–1.70 (m, 2H), 1.74–2.04 (m, 7H), 2.18–2.40 (m, 1H), 2.24 (brs, 3H), 3.22–3.92 (m, 5H), 3.82 (brs, 6H), 4.70–4.80 (m, 1H), 5.10 (brs, 2H), 6.08 (brs, 1H), 6.69–6.84 (m, 3H)

No. 45
¹HNMR (CDCl₃) δppm: 1.50–1.69 (m, 2H), 1.75–2.03 (m, 7H), 2.18–2.30 (m, 1H), 3.23–3.93 (m, 5H), 3.82 (s, 3H), 4.70–4.80 (m, 1H), 5.02 (brs, 2H), 6.46 (m, 1H), 6.70–6.84 (m, 3H), 7.39 (m, 1H), 7.48 (m, 1H)

No. 46
¹HNMR (CDCl₃) δppm: 1.56–2.12 (m, 9H), 2.22–2.38 (m, 1H), 3.30–3.58 (m, 3H), 3.68–3.96 (m, 2H), 3.84 (s, 3H), 4.74–4.80 (m, 1H), 5.27 (brs, 2H), 6.76–6.85 (m, 3H), 8.02 (m, 1H), 8.17–8.19 (m, 1H), 8.41–8.43 (m, 1H)

EMBODIMENT 4

Preparation of (+)-3-(3-cyclopentyloxy-4-methoxyphenyl)-1-(3-pyridylmethoxycarbonyl) pyrrolidine and (−)-3-(3-cyclopentyloxy-4-methoxyphenyl)-1-(3-pyridylmethoxycarbonyl) pyrrolidine:

145 mg of (±)-3-(3-cyclopentyloxy-4-methoxyphenyl)-1-(3pyridylmethoxycarbonyl) pyrrolidine (Compound No. 13 in Table 1) was separated with HPLC (eluent: ethanol/hexane=10/90) using the optical isomer separation column CHIRALPAKAS (Daicel xxx) to obtain (+)-3-(3-cyclopentyloxy-4-methoxyphenyl)-1-(3 -pyridylmethoxycarbonyl) pyrrolidine (Compound No. 47) 64 mg $[\alpha]_D^{25}=+22.3°$ (c0.91, methanol), and (−)-3-(3-cyclopentyloxy-4-methoxyphenyl)-1-(3-pyridylmethoxycarbonyl) pyrrolidine (Compound No. 48) 61 mg $[\alpha]_D^{25}=-23.7°$ (c1.02, methanol).

EMBODIMENT 5

Compounds shown in Table 1 (shown hereinbelow) were synthesized according to the methods in Embodiments 1 and 2.

TABLE 1

| compound No. | R¹ | R² | —A—Y—R³ | physical properties |
|---|---|---|---|---|
| 49 | Me |  | 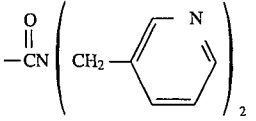 | oily matter |
| 50 | Me |  | 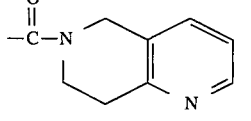 | oily matter |
| 51 | Me |  | 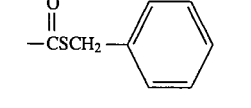 | oily matter |
| 52 | Me |  | 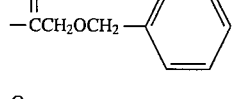 | oily matter |
| 53 | Me |  | 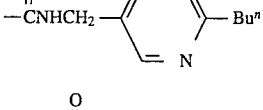 | oily matter |
| 54 | Me |  | 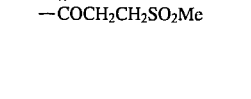 | oily matter |

TABLE 1-continued

| compound No. | R¹ | R² | —A—Y—R³ | physical properties |
|---|---|---|---|---|
| 55 | Me | cyclopentyl | $-\overset{O}{\underset{\|}{C}}N(COCH_3)CH_2$-(3-pyridyl) | oily matter |
| 56 | Me | cyclopentyl | $-\overset{O}{\underset{\|}{C}}NHCH_2$-(2-pyridyl) | oily matter |
| 57 | Me | cyclopentyl | $-\overset{O}{\underset{\|}{C}}NHCH_2CH_2$-(2-pyridyl) | oily matter |
| 58 | Me | cyclopentyl | pyrrolidinyl-CO- attached to 4-methoxy-3-cyclopentyloxyphenyl | mp 120–123° C. |
| 59 | Me | cyclopentyl | $-\overset{O}{\underset{\|}{C}}NH$-(3-pyridyl) | oily matter |
| 60 | Me | cyclopentyl | $-\overset{O}{\underset{\|}{C}}NHCH_2CH_2$-(indol-3-yl) | oily matter |
| 61 | Me | cyclopentyl | $-\overset{O}{\underset{\|}{C}}NHCH_2$-(2-furyl) | mp 93–95° C. |
| 62 | Me | cyclopentyl | $-\overset{O}{\underset{\|}{C}}NHCH_2CH_2$-(1-methylpyrrol-2-yl) | oily matter |
| 63 | Me | cyclopentyl | $-\overset{O}{\underset{\|}{C}}NHCH_2$-(2-thienyl) | amorphous solid |
| 64 | Me | cyclopentyl | $-\overset{O}{\underset{\|}{C}}NH$-(3,5-dichloropyridin-4-yl) | amorphous solid |

In Table 1, Me represents methyl, Et ethyl, Bu\ n-butyl and Bu\ tert-butyl.

No. 49
¹HNMR (CDCl₃) δppm: 1.50–2.10 (m, 9H), 2.20–2.38 (m, 1H), 3.2–3.7 (m, 4H), 3.8 (m, 1H), 3.82 (s, 3H), 4.23–4.57 (m, 4H), 4.60–4.83 (m, 1H), 6.63–6.93 (m, 3H), 7.20–7.40 (m, 2H), 7.57–7.76 (m, 2H), 8.40–8.68 (m, 4H)
No. 50

¹HNMR (CDCl₃) δppm: 1.49–2.10 (m, 9H), 2.20–2.36 (m, 1H), 2.9–3.8 (m, 9H), 3.83 (s, 3H), 4.73 (s, 2H), 4.70–4.80 (m, 1H), 6.70–6.85 (m, 3H), 6.80 (dd, 1H), 7.41 (d, 1H), 8.43 (d, 1H)

No. 51
¹HNMR (CDCl₃) δppm: 1.49–1.71 (m, 2H), 1.74–2.09 (m, 7H), 2.20–2.36 (m, 1H), 3.2–4.1 (m, 5H), 3.82 (s, 3H), 4.20 (s, 2H), 4.69–4.79 (m, 1H), 6.69–6.84 (m, 3H), 7.19–7.41 (m, 5H)

No. 52
¹HNMR (CDCl₃) δppm: 1.53–1.70 (m, 2H), 1.75–2.08 (m, 7H), 2.20–2.38 (m, 1H), 3.2–4.1 (m, 5H), 3.82 (s, 3H), 4.13 (m, 2H), 4.65 (m, 2H), 4.70–4.80 (m, 1H), 6.70–6.85 (m, 3H), 7.25–7.43 (m, 5H)

No. 53
¹HNMR (CDCl₃) δppm: 0.94 (t, 3H), 1.39 (m, 2H), 1.51–2.09 (m, 11H), 2.23–2.35 (m, 1H), 2.77 (t, 2H), 3.25–3.48 (m, 3H), 3.55–3.66 (m, 1H), 3.8 (m, 1H), 3.83 (s, 3H), 4.44 (d, 2H), 4.53 (t, 1H), 4.69–4.79 (m, 1H), 6.73–6.85 (m, 3H), 7.11 (d, 1H), 7.60 (dd, 1H), 8.44 (d, 1H)

No. 54
¹HNMR (CDCl₃) δppm: 1.53–1.70 (m, 2H), 1.75–2.08 (m, 7H), 2.19–2.35 (m, 1H), 3.00 (m, 3H), 3.20–3.51 (m, 5H), 3.55–3.90 (m, 2H), 3.83 (s, 3H), 4.57 (m, 2H), 4.70–4.81 (m, 1H), 6.70–6.85 (m, 3H)

No. 55
¹HNMR (CDCl₃) δppm: 1.52–1.74 (m, 2H), 1.75–2.07 (m, 7H), 2.17 (s, 3H), 2.20–2.38 (m, 1H), 3.1–3.9 (m, 5H), 3.83 (s, 3H), 4.63–4.93 (m, 3H), 6.54–6.84 (m, 3H), 7.27 (m, 1H), 7.75 (m, 1H), 8.47–8.63 (m, 2H)

No. 56
¹HNMR (CDCl₃) δppm: 1.47–1.74 (m, 2H), 1.74–2.10 (m, 7H), 2.18–2.37 (m, 1H), 3.18–3.53 (m, 3H), 3.58–3.94 (m, 2H), 3.80 (s, 3H), 4.54 (d, 2H), 4.70–4.80 (m, 1H), 5.84 (t, 1H), 6.73–6.83 (m, 3H), 7.15 (m, 1H), 7.30 (m, 1H), 7.62 (m, 1H), 8.49 (m, 1H)

No. 57
¹HNMR (CDCl₃) δppm: 1.50–1.70 (m, 2H), 1.72–2.04 (m, 7H), 2.18–2.34 (m, 1H), 3.01 (t, 2H), 3.22–3.85 (m, 7H), 3.83 (s, 3H), 4.68–4.79 (m, 1H), 5.34 (t, 1H), 6.73–6.83 (m, 3H), 7.08–7.20 (m, 2H), 7.57–7.64 (m, 1H), 8.50 (m, 1H)

No. 59
¹HNMR (CDCl₃) δppm: 1.47–2.15 (m, 9H), 2.22–2.42 (m, 1H), 3.28–4.03 (m, 5H), 3.83 (s, 3H), 4.70–4.80 (m, 1H), 6.61 (bs, 1H), 6.75–6.85 (m, 3H), 7.22 (m, 1H), 8.09 (m, 1H), 8.24 (m, 1H), 8.48 (m, 1H)

No. 60
¹HNMR (CDCl₃) δppm: 1.48–1.70 (m, 2H), 1.70–2.05 (m, 7H), 2.16–2.33 (m, 1H), 2.98 (t, 2H), 3.16–3.33 (m, 3H), 3.45–3.75 (m, 4H), 3.81 (s, 3H), 4.37 (t, 1H), 4.70–4.80 (m, 1H), 6.65–6.95 (m, 3H), 7.00 (m, 1H), 7.06–7.23 (m, 2H), 7.35 (m, 1H), 7.62 (m, 1H), 8.67 (bs, 1H)

No. 62
¹HNMR (CDCl₃) δppm: 1.50–1.70 (m, 2H), 1.75–2.05 (m, 7H), 2.18–2.35 (m, 1H), 2.81 (t, 2H), 3.23–3.55 (m, 6H), 3.59 (s, 3H), 3.70–3.87 (m, 1H), 3.83 (s, 3H), 4.45 (t, 1H), 4.70–4.80 (m, 1H), 5.92 (m, 1H), 6.05 (m, 1H), 6.57 (m, 1H), 6.73–6.83 (m, 3H)

No. 63
¹HNMR (CDCl₃) δppm: 1.52–1.70 (m, 2H), 1.74–2.07 (m, 7H), 2.18–2.39 (m, 1H), 3.3–3.8 (m, 5H), 3.83 (s, 3H), 4.56 (m, 1H), 4.63 (d, 2H), 4.70–4.80 (m, 1H), 6.73–6.83 (m, 3H), 6.92–7.00 (m, 2H), 7.22 (m, 1H)

No. 64
¹HNMR (CDCl₃) δppm: 1.53–1.72 (m, 2H), 1.75–2.23 (m, 7H), 2.30–2.47 (m, 1H), 3.47–3.66 (m, 3H), 3.79 (m, 1H), 3.84 (s, 3H), 3.98 (m, 1H), 4.73–4.83 (m, 1H), 6.27 (bs, 1H), 6.78–6.86 (m, 3H), 8.48 (s, 2H)

Hereinbelow, compounds which can be synthesized according to the methods of Embodiments 1 and 2 will be shown in Table 2.

TABLE 2

| compound No. | Y | n | X |
|---|---|---|---|
| 65 | —O— | 2 | 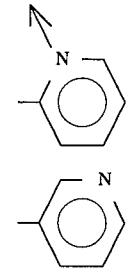 |
| 66 | —O— | 2 | 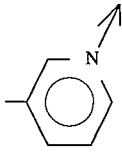 |
| 67 | —O— | 2 | 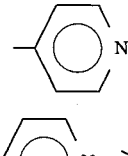 |
| 68 | —O— | 2 | 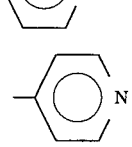 |
| 69 | —O— | 2 |  |
| 70 | —NH— | 1 | 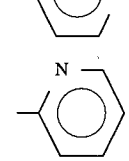 |
| 71 | —NH— | 2 | 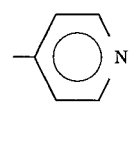 |
| 72 | —NH— | 2 | |
| 73 | —NMe— | 1 | |
| 74 | —NMe— | 1 |  |

TABLE 2-continued
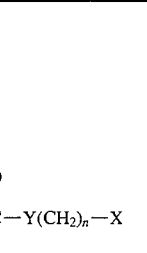
| compound No. | Y | n | X |
|---|---|---|---|
| 75 | —NMe— | 2 | 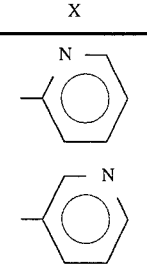 |
| 76 | —NMe— | 2 |  |
| 77 | —NMe— | 2 | 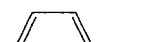 |
| 78 | —O— | 1 | 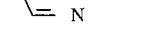 OMe |
| 79 | —O— | 2 | 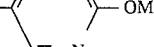 OMe |
| 80 | —O— | 1 |  OEt |
| 81 | —O— | 2 | 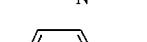 OEt |
| 82 | —O— | 1 | 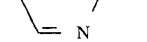 OPr |
| 83 | —O— | 2 |  OPr |
| 84 | —O— | 1 | 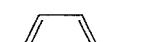 OBu |
| 85 | —O— | 2 | 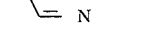 OBu |
| 86 | —NH— | 1 | 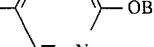 OMe |
| 87 | —NH— | 2 | OMe |
| 88 | —NH— | 1 | OEt |
| 89 | —NH— | 2 | OEt |
| 90 | —NH— | 1 | OPr |
| 91 | —NH— | 2 | OPr |
| 92 | —NH— | 1 | OBu |
| 93 | —NH— | 2 | OBu |
| 94 | —NMe— | 1 | OMe |
| 95 | —NMe— | 2 | OMe |
| 96 | —NMe— | 1 | OEt |

TABLE 2-continued

[Structure: MeO and cyclopentyloxy substituted phenyl attached to pyrrolidine with N-C(=O)-Y(CH₂)ₙ-X]

| compound No. | Y | n | X |
|---|---|---|---|
| 97 | —NMe— | 2 | 2-ethoxypyridin-5-yl |
| 98 | —NMe— | 1 | 2-propoxypyridin-5-yl |
| 99 | —NMe— | 2 | 2-propoxypyridin-5-yl |
| 100 | —NMe— | 1 | 2-butoxypyridin-5-yl |
| 101 | —NMe— | 2 | 2-butoxypyridin-5-yl |
| 102 | —O— | 2 | pyridazin-3-yl |
| 103 | —O— | 1 | pyridazin-4-yl |
| 104 | —O— | 2 | pyridazin-4-yl |
| 105 | —O— | 2 | pyrazin-2-yl |
| 106 | —O— | 1 | pyrazin-2-yl N-oxide |
| 107 | —O— | 2 | pyrazin-2-yl N-oxide |
| 108 | —O— | 2 | pyrazin-2-yl N,N'-dioxide |
| 109 | —O— | 1 | pyrazin-2-yl N,N'-dioxide |
| 110 | —O— | 2 | pyrazin-2-yl N,N'-dioxide |
| 111 | —O— | 1 | pyrimidin-2-yl |
| 112 | —O— | 2 | pyrimidin-2-yl |
| 113 | —O— | 1 | pyrimidin-4-yl |
| 114 | —O— | 2 | pyrimidin-4-yl |

TABLE 2-continued

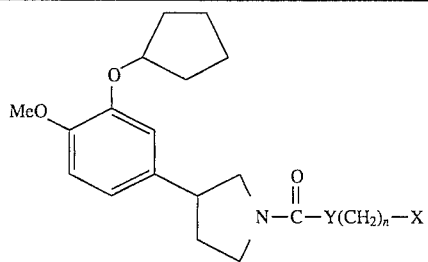

| compound No. | Y | n | X |
|---|---|---|---|
| 115 | —O— | 1 | pyrimidine |
| 116 | —O— | 2 | pyrimidine |
| 117 | —NH— | 1 | pyridazine |
| 118 | —NH— | 2 | pyridazine |
| 119 | —NH— | 1 | pyridazine |
| 120 | —NH— | 2 | pyridazine |
| 121 | —NH— | 1 | pyrazine |
| 122 | —NH— | 2 | pyrazine |
| 123 | —NH— | 1 | pyrimidine |
| 124 | —NH— | 2 | pyrimidine |
| 125 | —NH— | 1 | pyrimidine |

TABLE 2-continued

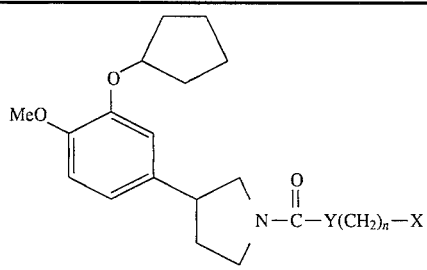

| compound No. | Y | n | X |
|---|---|---|---|
| 126 | —NH— | 2 | pyrimidine |
| 127 | —NH— | 1 | pyrimidine |
| 128 | —NH— | 2 | pyrimidine |
| 129 | —NMe— | 1 | pyridazine |
| 130 | —NMe— | 2 | pyridazine |
| 131 | —NMe— | 1 | pyridazine |
| 132 | —NMe— | 2 | pyridazine |
| 133 | —NMe— | 1 | pyrazine |
| 134 | —NMe— | 2 | pyrazine |
| 135 | —NMe— | 1 | pyrimidine |
| 136 | —NMe— | 2 | pyrimidine |

TABLE 2-continued

Structure: MeO and cyclopentyloxy substituted phenyl attached to pyrrolidine with N—C(=O)—Y(CH$_2$)$_n$—X

| compound No. | Y | n | X |
|---|---|---|---|
| 137 | —NMe— | 1 | pyrazine (N at 1,4) |
| 138 | —NMe— | 2 | pyrazine (N at 1,4) |
| 139 | —NMe— | 1 | pyrimidine |
| 140 | —NMe— | 2 | pyrimidine |

In Table 2, Me represents methyl, Et ethyl, Pr propyl and Bu butyl.

EMBODIMENT 6

Preparation of Tablet:

1000 g of well crushed 3-(3-cyclopentyloxy-4-methoxyphenyl)-1-(3-pyridylmethoxycarbonyl) pyrrolidine hydrochloride (Compound No. 15 in Table 1), 5900 g of lactose, 2000 g of crystal cellulose, 1000 g of low-degree substitution hydroxypropylcellulose and 100 g of magnesium stearate are well mixed so as to produce bare tablets containing 10 mg of the foregoing compound in one tablet of 100 mg using the direct tablet making method. By applying sugar-coating or film-coating to the bare tablets, the sugar-coated tablets or the film-coated tablets were produced.

EMBODIMENT 7

Preparation of Capsule Medicine 1000 g of well crushed 3-(3-cyclopentyloxy-4-methoxyphenyl)-1-(3-pyridylmethoxycarbonyl) pyrrolidine p-toluenesulfonate (Compound No. 14 in Table 1), 3000 g of corn starch, 6900 g of lactose, 1000 g of crystal cellulose and 100 g of magnesium stearate were mixed to produce capsule medicine containing 10 mg of the foregoing compound in one capsule of 120 mg.

EMBODIMENT 8

Preparation of Inhalation Medicine 5 g of well crushed 3-(3-cyclopentyloxy-4-methoxyphenyl)-1-(3-pyridylmethylaminocarbonyl) pyrrolidine (Compound No. 22 in Table 1), log of medium-chain saturated fatty acid triglyceride and 0.2 g of (sorbitan xxx) were well mixed. Subsequently, a mixture of 15.2 mg was weighed into each aluminum container of 5 ml for aerosol. Further, a mixture of freon 12 and 114, in the ratio of 1:1, of 8.48 mg at a low temperature was filled into each container. Thereafter, an adaptor for metering 10.0 ml per injection was attached to the container to produce inhalation medicine containing 5 mg of the foregoing compound in one spray-type container of 5 ml. For showing availability of the compounds of the present invention, the results of the pharmacological tests of the compounds will be given hereinbelow.

(roliplum xxx) in Table 3 is the compound represented by the foregoing structure as described in the foregoing Japanese First Patent Publication No. 50-157360. In, for example, Adv. Second Messenger Phosphoprotein Res., 22, 1 (1988), it is described to show specific inhibition to PDE IV.

Test 1

Action to Phosphodiesterase (PDE) IV Enzyme Activities

Enzyme was partialy purified from human histiocytic lymphoma(U-937) cytoplasm fraction by means of the Q-sepharose column according to the method of Nicholson and collaborators [Br. J. Pharmacol., 97, 889 (1989)], and was reacted in a solution of 0.1 mg/ml BSA (bovine serum albumin), 1 mM EDTA (ethylenediaminetetra acetic acid), 5 mM MgCl$_2$ and 50 mM Tris-buffer (pH 8.0) for 15 minutes at 30° C. using 0.4 μM $^3$H-cAMP as substrate according to the method of Hidaka and collaborators [Biochem. Med., 10, 301 (1974)]. $^3$H-5'-AMP generated was separated by means of the cation exchange column, and the enzyme activity was determined by measuring a radioactivity amount.

A test compound was added. After incubation for 15 minutes at 30° C., the substrate was added. Inhibition ratios were derived for respective concentrations assuming that the reaction without the test compound was 100%. By using the probit analysis, the concentration (IC$_{50}$) showing the inhibition rate of 50% was derived. The results are shown in Table 3.

TABLE 3

| compound No. | PDE IV inhibitory activity IC$_{50}$(M) |
|---|---|
| 1 | $1.0 \times 10^{-8}$ |
| 3 | $6.0 \times 10^{-9}$ |
| 4 | $1.1 \times 10^{-8}$ |
| 6 | $6.0 \times 10^{-9}$ |
| 7 | $2.0 \times 10^{-8}$ |
| 8 | $1.9 \times 10^{-8}$ |
| 13 | $3.3 \times 10^{-9}$ |
| 17 | $2.3 \times 10^{-8}$ |
| 19 | $3.8 \times 10^{-9}$ |
| 23 | $1.4 \times 10^{-8}$ |
| 24 | $2.3 \times 10^{-9}$ |
| 26 | $8.8 \times 10^{-9}$ |
| 32 | $2.5 \times 10^{-8}$ |
| 36 | $1.1 \times 10^{-8}$ |
| 37 | $1.9 \times 10^{-8}$ |
| 38 | $2.3 \times 10^{-8}$ |
| 40 | $1.0 \times 10^{-8}$ |
| 42 | $8.0 \times 10^{-9}$ |
| 48 | $1.1 \times 10^{-9}$ |
| roliplam | $3.0 \times 10^{-7}$ |

What we claim is:

1. A 3-phenylpyrrolidine compound of the formula

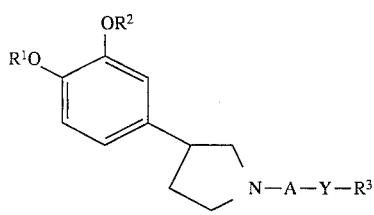

wherein $R^1$ is $C_1$–$C_4$ alkyl;

$R^2$ is tetrahydrofuranyl, $C_1$–$C_7$ alkyl, $C_1$–$C_7$ haloalkyl, $C_2$–$C_7$ alkenyl, bicyclo [2.2.1]hept-2-yl or $C_3$–$C_8$ cycloalkyl;

A is

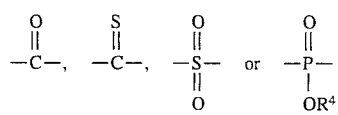

wherein $R^4$ is $C_1$–$C_4$ alkyl;

Y is —O—, —S—, —O—N=CH— or $NR^5$— wherein $R^5$ is hydrogen, $C_1$–$C_4$ alkyl, $C_2$–$C_4$ alkylcarbonyl or pyridylmethyl, or a single bond;

$R^3$ is (a) $C_1$–$C_7$ alkyl which is unsubstituted or substituted by one or more substituents, or (b) —$(CH_2)_n$—X wherein n is an integer of 0 to 4, and X is phenyl which is unsubstituted or substituted by one or more substituents, naphthyl which is unsubstituted or substituted by one or more substituents or a heterocyclic ring system which is unsubstituted or substituted by one or more substituents;

with the proviso that when —A—Y—$R^3$ is

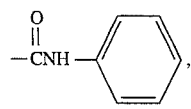

$R^1$ and $R^2$ are not simultaneously methyl;

an optical isomer, a salt, an N-oxide compound, a hydrate or a solvate thereof.

2. A compound as claimed in claim 1 wherein $R^1$ is methyl and $R^2$ is cyclopentyl.

3. A compound as claimed in claim 1 wherein $R^3$ is —$(CH_2)_n$—X wherein n is an integer of 0 to 2 and X is a heterocyclic ring system which is unsubstituted or substituted by one or more substituents.

4. A compound as claimed in claim 1 wherein $R^3$ is —$(CH_2)_n$—X wherein n is 1 or 2 and X is a heterocyclic ring system having a ring of 6 atoms including 1 or 2 nitrogen atoms.

5. A compound as claimed in claim 1 wherein A is

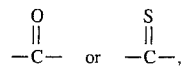

Y is —O—, —S—, —$NR^5$— wherein $R^5$ is hydrogen, $C_1$–$C_4$ alkyl, $C_2$–$C_4$ alkylcarbonyl or pyridylmethyl, or a single bond.

6. A compound as claimed in claim 1 wherein A is

Y is —O— or —$NR^5$— wherein $R^5$ is hydrogen, $C_1$–$C_4$ alkyl, $C_2$–$C_4$ alkylcarbonyl or pyridylmethyl.

7. A pharmaceutical composition comprising a compound as claimed in claim 1 as an active ingredient together with a pharmaceutically acceptable carrier therefor.

8. A pharmaceutical composition useful as an antiasthmatic comprising a compound as claimed in claim 1 as an active ingredient together with a pharmaceutically acceptable carrier therefor.

* * * * *